United States Patent
Alshafei et al.

(10) Patent No.: US 10,906,026 B2
(45) Date of Patent: Feb. 2, 2021

(54) METHODS OF MAKING SPRAY-DRIED METATHESIS CATALYSTS AND USES THEREOF

(71) Applicant: Saudi Arabian Oil Company, Dhahran (SA)

(72) Inventors: Faisal H. Alshafei, Khobar (SA); Munir D. Khokhar, Al-Khobar (SA); Sohel K. Shaikh, Dhahran (SA); Mohammed R. Alalouni, Dammam (SA); Gopal Juttu, Dhahran (SA)

(73) Assignee: SAUDI ARABIAN OIL COMPANY

( * ) Notice: Subject to any disclaimer, the term of this patent is extended or adjusted under 35 U.S.C. 154(b) by 106 days.

(21) Appl. No.: 16/169,427

(22) Filed: Oct. 24, 2018

(65) Prior Publication Data
US 2019/0118164 A1    Apr. 25, 2019

Related U.S. Application Data

(60) Provisional application No. 62/576,376, filed on Oct. 24, 2017.

(51) Int. Cl.
*B01J 23/30* (2006.01)
*B01J 21/08* (2006.01)
(Continued)

(52) U.S. Cl.
CPC .............. *B01J 23/30* (2013.01); *B01J 21/08* (2013.01); *B01J 35/002* (2013.01);
(Continued)

(58) Field of Classification Search
CPC . B01J 23/30; B01J 21/08; B01J 35/002; B01J 37/0045; B01J 37/0219; B01J 37/04; B01J 13/043; C07C 4/06; C07C 6/04; C07C 11/04; C07C 11/06; C07C 11/10; C07C 11/107; C07C 2521/08; C07C 2523/30
(Continued)

(56) References Cited

U.S. PATENT DOCUMENTS 3,956,474 A   5/1976   Ritsko
4,198,319 A   4/1980   Alafandi et al.
(Continued)

FOREIGN PATENT DOCUMENTS

WO   2006060354 A1   6/2006
WO   2006089957 A1   8/2006
WO   2017003821 A1   1/2017

OTHER PUBLICATIONS

The International Search Report and Written Opinion for related PCT application PCT/US2018/056999 dated Jan. 11, 2019.
(Continued)

*Primary Examiner* — Patricia L. Hailey
(74) *Attorney, Agent, or Firm* — Bracewell LLP; Constance R. Rhebergen

(57) ABSTRACT

Provided here are catalyst compositions containing tungsten oxide on silica supports and prepared by spray drying a mixture containing a tungsten precursor, silica support, and a surfactant. Also provided here are methods of using the catalytic compositions, prepared by spray drying, in an olefin metathesis process to produce propylene from butenes.

20 Claims, 6 Drawing Sheets
(1 of 6 Drawing Sheet(s) Filed in Color)

(51) Int. Cl.
  *B01J 37/00* (2006.01)
  *B01J 37/04* (2006.01)
  *C07C 4/06* (2006.01)
  *C07C 6/04* (2006.01)
  *B01J 37/02* (2006.01)
  *B01J 35/00* (2006.01)
  *C07C 11/107* (2006.01)
  *C07C 11/06* (2006.01)
  *C07C 11/04* (2006.01)
  *C07C 11/10* (2006.01)

(52) U.S. Cl.
  CPC ....... *B01J 37/0045* (2013.01); *B01J 37/0219* (2013.01); *B01J 37/04* (2013.01); *C07C 4/06* (2013.01); *C07C 6/04* (2013.01); *C07C 11/04* (2013.01); *C07C 11/06* (2013.01); *C07C 11/10* (2013.01); *C07C 11/107* (2013.01); *C07C 2521/08* (2013.01); *C07C 2523/30* (2013.01)

(58) Field of Classification Search
  USPC .................................................. 502/254, 305
  See application file for complete search history.

(56) References Cited

U.S. PATENT DOCUMENTS

| | | | | |
|---|---|---|---|---|
| 4,575,575 A | * | 3/1986 | Drake | B01J 23/30 585/646 |
| 5,030,780 A | * | 7/1991 | Ward | B01J 29/16 208/143 |
| 5,834,394 A | * | 11/1998 | Chen | C07C 253/18 502/302 |
| 6,518,349 B1 | | 2/2003 | Felix et al. | |
| 6,586,649 B1 | | 7/2003 | Botha et al. | |
| 6,752,979 B1 | * | 6/2004 | Talbot | C01B 13/18 423/592.1 |
| 6,960,556 B2 | | 11/2005 | Gingerich | |
| 7,754,647 B2 | | 7/2010 | Schubert et al. | |
| 7,960,308 B2 | | 6/2011 | Fukumoto | |
| 8,440,874 B2 | | 5/2013 | Ramachandran et al. | |
| 9,234,060 B2 | | 1/2016 | Kao et al. | |
| 10,010,870 B2 | * | 7/2018 | Ostraat | C07C 6/04 |
| 2008/0004462 A1 | | 1/2008 | Peters et al. | |
| 2011/0196185 A1 | | 8/2011 | Krawczyk et al. | |
| 2012/0283090 A1 | | 11/2012 | Popp et al. | |
| 2013/0090511 A1 | * | 4/2013 | Soultanidis | B01J 21/08 585/653 |
| 2014/0005031 A1 | * | 1/2014 | Chaumonnot | B01J 27/186 502/64 |
| 2014/0179973 A1 | * | 6/2014 | Debecker | B01J 27/19 585/644 |
| 2017/0001925 A1 | * | 1/2017 | Abudawoud | B01J 37/0201 |

OTHER PUBLICATIONS

Debecker et al., "Aerosol route to nanostructured WO3—SiO2—Al2O3 metathesis catalysts: Toward higher propene yield", Applied Catalysis A: General, 2014, pp. 458-466, Elsevier.

Maksasithorn et al., "Preparation of super-microporous WO3—SiO2 olefin metathesis catalysts by the aerosol-assisted sol-gel process", Microporous and Mesoporous Materials, 2015, pp. 125-133, Elsevier.

\* cited by examiner

METHODS OF MAKING SPRAY-DRIED METATHESIS CATALYSTS AND USES THEREOF

CROSS-REFERENCE TO RELATED APPLICATIONS

This application claims the benefit of U.S. Provisional Application No. 62/576,376, filed Oct. 24, 2017, which is incorporated by reference herein in its entirety.

TECHNICAL FIELD

The disclosure relates to the methods of making and using spray-dried catalysts for olefin metathesis and also describes systems for olefin metathesis using these spray-dried catalysts.

BACKGROUND

Commercial demand for polypropylene, acetone, propylene oxide, glycols, cumene, acrylonitrile, and acrylic acid has been growing in recent years. Most of the propylene produced in the world is a byproduct of steam crackers and fluid catalytic cracking units. The unprecedented growth in demand for propylene derivatives and the changing feedstock of steam crackers from naphtha to ethane changed the supply-demand dynamics and resulted in a supply gap, which led to the development of on-purpose propylene production technologies. Olefin metathesis is an on-purpose propylene production technology that shifts the composition pool of low-value butenes to high-value propylene. The metathesis of butenes especially 2-butene while managing ethylene is a challenging process. Further challenges include maintaining or reducing the production of byproducts such as pentene and hexene, which are co-produced in the self- and cross-metathesis reactions of butenes, and increasing propylene production from the butene feeds.

SUMMARY

Several disadvantages in the olefin metathesis methods were recognized by the inventors and various embodiments of this disclosure were developed to address these shortcomings in the art. Certain embodiments include catalytic compositions containing spray-dried tungsten oxide on silica support. Also disclosed are methods for the preparation of spray-dried metathesis catalysts.

One such method for the preparation of spray-dried metathesis catalysts includes the steps of combining a tungsten precursor with a surfactant to form a first mixture, contacting the first mixture with a second mixture containing a silica support under conditions of constant stirring to form a third mixture containing the tungsten precursor loaded on the silica support, and subjecting the third mixture to a spray drying process to obtain a spray-dried metathesis catalyst. In certain embodiments, the spray drying process can include supplying the third mixture to a spray dryer at a temperature ranging from 250 degrees Celsius (° C.) to 300° C. The silica support can include preformed silica particles. The surfactant can be a poly(ethylene glycol)-block-poly(propylene glycol)-block-poly(ethylene glycol) copolymer. The tungsten precursor can be ammonium metatungstate or ammonium paratungstate. The amount of tungsten oxide loaded on the silica support of the spray-dried metathesis catalyst can range from 2 to 25 weight percent (wt %). In certain embodiments, the amount of tungsten oxide loaded on the silica support of the spray-dried metathesis catalyst can range from 6 to 15 weight percent. In certain embodiments, the amount of tungsten oxide loaded on the silica support of the spray-dried metathesis catalyst is about 6 weight percent.

Certain embodiments include methods for production of propylene using the spray-dried metathesis catalysts. One such method for production of propylene includes the steps of contacting a hydrocarbon feedstock containing butenes under metathesis reaction conditions with a catalyst containing tungsten oxide on a silica support to produce a product stream containing propylene, and then, fractionating the product stream to form a propylene-rich stream. This catalyst has been prepared by a spray drying process. The spray drying process can include contacting the silica support with a tungsten precursor in the presence of a surfactant. The silica support can include preformed silica particles. The surfactant can be a poly(ethylene glycol)-block-poly(propylene glycol)-block-poly(ethylene glycol) copolymer. The tungsten precursor can be ammonium metatungstate or ammonium paratungstate. The amount of tungsten oxide loaded on the silica support of the spray-dried metathesis catalyst can range from 2 to 25 wt %. In other embodiments, the amount of tungsten oxide loaded on the silica support of the spray-dried metathesis catalyst can range from 6 to 15 wt %. In other embodiments, the amount of tungsten oxide loaded on the silica support of the spray-dried metathesis catalyst is about 6 wt %. The hydrocarbon feedstock contains 2-butene. In certain embodiments, the tungsten oxide on silica support catalyst composition is pretreated by exposure to nitrogen gas before being contacted with the hydrocarbon feedstock.

Numerous other aspects, features and benefits of the present disclosure may be made apparent from the following detailed description taken together with the drawings. The methods can include other steps or additional components depending on desired goals.

BRIEF DESCRIPTION OF THE DRAWINGS

The patent application contains at least one drawing executed in color. Copies of this patent or patent application publication with color drawing(s) will be provided by the Office upon request and payment of the necessary fee.

Embodiments will be readily understood by the following detailed description in conjunction with the accompanying figures. Embodiments are illustrated by way of example and not by way of limitation in the accompanying figures, as the disclosure may include other effective embodiments as well.

DETAILED DESCRIPTION

Figure 1:
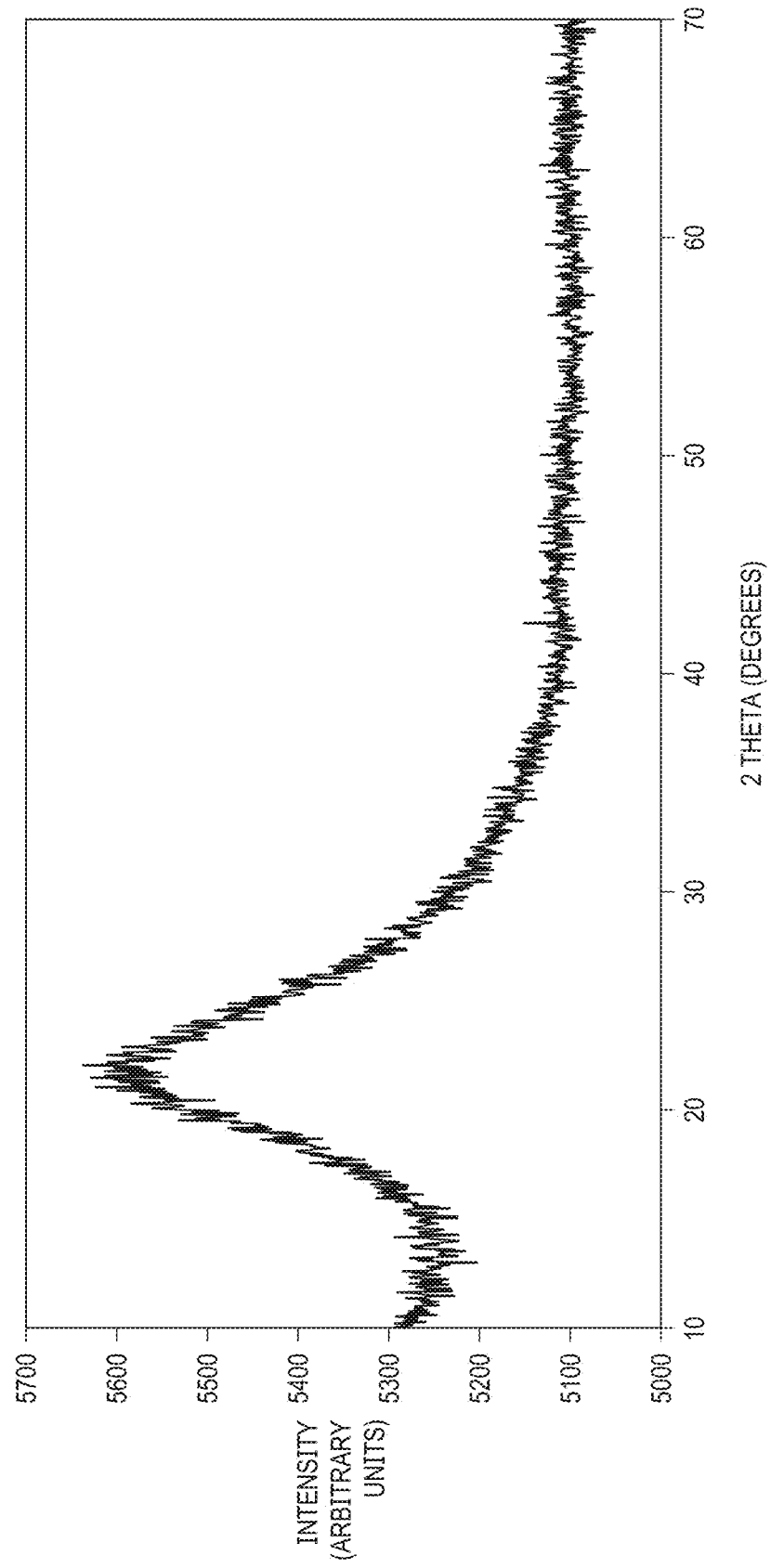
FIG. 1 is the X-ray diffraction (XRD) pattern obtained following the analysis of the silica support without any tungsten oxide.

The disclosure describes various compositions of spray-dried metathesis catalysts and methods of preparation of these compositions, and methods of use of these compositions for converting butene to propylene. In the following description, numerous details are set forth in order to provide a thorough understanding of the various embodiments. In other instances, well-known processes, devices, and systems may not been described in particular detail in order not to unnecessarily obscure the various embodiments. Additionally, illustrations of the various embodiments may omit certain features or details in order to not obscure the various embodiments.

In the following detailed description, reference is made to the accompanying drawings that form a part of this disclosure. The drawings provide an illustration of some of the various embodiments in which the subject matter of the present disclosure may be practiced. Other embodiments may be utilized, and logical changes may be made without departing from the scope of this disclosure. The description may use the phrases "in certain embodiments," "in various embodiments," "in an embodiment," or "in embodiments," which may each refer to one or more of the same or different embodiments. Furthermore, the terms "comprising," "including," "having," "containing," and the like, as used with respect to embodiments of the present disclosure, are synonymous. The term "about" or "approximately" means within an acceptable error range for the particular value as determined by one of ordinary skill in the art, which will depend in part on how the value is measured or determined, namely the limitations of the measurement system. For example, "about" with respect to the compositions or reaction conditions or physical properties of compositions can mean plus or minus a range of up to 20%, preferably up to 10%, more preferably up to 5%.

Embodiments include methods for the preparation of a spray-dried metathesis catalyst. One such method includes combining a tungsten precursor with a surfactant to form a first mixture, contacting the first mixture with a second mixture containing a silica support under conditions of constant stirring to form a third mixture containing the tungsten precursor loaded on the silica support, and subjecting the third mixture to a spray drying process to obtain a spray-dried metathesis catalyst. The spray drying process can include supplying the third mixture to a spray dryer at a temperature ranging from 250° C. to 300° C. Preformed silica particles can be used as the silica support to prepare the catalyst composition. In certain embodiments, the surfactant is a symmetric triblock copolymer. The surfactant can be a poly(ethylene glycol)-block-poly(propylene glycol)-block-poly(ethylene glycol) copolymer. The tungsten precursor can be ammonium metatungstate or ammonium paratungstate. Other tungsten precursors can be used as long as they convert to the appropriate polytungstate ($WO_x$) species under the thermal conditions described here. The amount of tungsten oxide loaded on the silica support of the spray-dried metathesis catalyst can range from about 2 to 25 weight percent. In certain embodiments, the amount of tungsten oxide loaded on the silica support of the spray-dried metathesis catalyst can range from about 6 to 15 weight percent. In certain embodiments, the amount of tungsten oxide loaded on the silica support of the spray-dried metathesis catalyst is about 6 weight percent.

Embodiments also include methods for the production of propylene by metathesis of butenes. One such method includes contacting a hydrocarbon feedstock containing butenes under metathesis reaction conditions with a catalyst containing tungsten oxide on a silica support to produce a product stream containing propylene, and then, fractionating the product stream to form a propylene-rich stream. The catalyst for this method is prepared by a spray drying process. In certain embodiments, the catalyst is pretreated by exposure to nitrogen gas before being contacted with the hydrocarbon feedstock. The hydrocarbon feedstock includes at least about 85 weight percent butenes. In certain embodiments, the hydrocarbon feedstock contains 2-butene. In certain embodiments, the hydrocarbon feedstock contains 1-butene. In certain embodiments, the hydrocarbon feedstock contains 1-butene and 2-butene. In certain embodiments, the feed contains a 50:50 mixture of cis- and trans-2-butene. In certain embodiments, butene in the feedstock is almost completely converted into propylene. In certain embodiments, preformed silica particles are used as the silica support. The spray drying process includes contacting the silica support with a tungsten precursor in the presence of a surfactant. In certain embodiments, the surfactant is a symmetric triblock copolymer. The surfactant can be a poly(ethylene glycol)-block-poly(propylene glycol)-block-poly(ethylene glycol) copolymer. The tungsten precursor can contain ammonium metatungstate or ammonium paratungstate. The amount of tungsten oxide loaded on the silica support of the spray-dried metathesis catalyst can range from about 2 to 25 weight percent. In certain embodiments, the amount of tungsten oxide loaded on the silica support of the spray-dried metathesis catalyst can range from about 6 to 15 weight percent. In certain embodiments, the amount of tungsten oxide loaded on the silica support of the spray-dried metathesis catalyst is about 6 weight percent.

As used in this disclosure, a "reactor" refers to a vessel in which one or more chemical reactions may occur between one or more reactants optionally in the presence of one or more catalysts. For example, a reactor may include a tank or tubular reactor configured to operate as a batch reactor, a continuous flow reactor, a continuous stirred-tank reactor, or a plug flow reactor. Examples of reactors include packed bed reactors such as fixed bed reactors and fluidized bed reactors. A reactor may contain one or more catalyst zones, such as catalyst beds. A zone is a whole or part of a working volume of a reactor, and a catalyst zone is configured to contain a catalyst. A reactor can have multiple zones and a reactor can therefore have multiple catalysts. In some embodiments, catalysts are placed in separate and defined zones such that the catalysts are homogeneous and not intermingled. In another embodiment, separation of components and reactions may take place in a reactive separation unit.

As used in this disclosure, a "catalyst" refers to a substance that increases the rate of a specific chemical reaction or increases the selective production of certain products in a reaction or both. Catalysts described in this disclosure may be utilized to promote various reactions, such as, but not limited to, metathesis reactions, cracking reactions, both metathesis reaction and cracking reaction, or isomerization reactions. For example, when the catalyst compositions described in this disclosure are utilized at elevated temperatures, butene isomerization reactions may occur, such as the conversion of 2-butenes to 1-butene or vice versa. These isomerization reactions can be part of the reactions that convert the feedstock to various $C_4$ compounds, such as 1-butene and isobutene. As used in this disclosure, a "metathesis catalyst" increases the rate of a metathesis reaction or increases the production of selective products of a metathesis reaction or both. As used in this disclosure "metathesis" generally refers to a chemical reaction where fragments of alkenes are redistributed by the scission and regeneration of alkene bonds. For example, a butene metathesis reaction involves two butene molecules reacting in the presence of a suitable catalyst to make propene or propylene. Other compounds that are produced as a result of side reactions are ethylene, pentenes, and hexenes.

Cross-Metathesis Reaction: 1-butene+2-butene↔propylene+2-pentene

Self-Metathesis Reaction: 1-butene+1-butene↔ethylene+3-hexene

Certain embodiments of the system involve utilizing a dual-bed catalyst system for the metathesis of a feed containing 1-butene. Certain embodiments of the system involve utilizing a dual-bed catalyst system for the metathesis of a feed containing 2-butene. In certain embodiments, the feed contains a 50:50 mixture of cis- and trans-2-butene. In the dual-bed catalyst system, the upstream bed of the catalyst zone contains a metathesis catalyst that metathesizes 2-butene to propylene. The metathesis catalyst in the upstream bed of the catalyst zone can be the catalyst composition containing tungsten oxide on silica support ($WO_3/SiO_2$) prepared by the spray drying method. The downstream bed of the catalyst zone contains a cracking catalyst that converts the byproducts, namely pentenes and hexenes, to yield more propylene.

Metathesis catalysts in the art are synthesized by conventional methods, such as wet impregnation and incipient wetness impregnation. Many metathesis catalysts that have been developed and tested including rhenium and molybdenum-based catalysts supported on zeolite supports or silica, alumina, or a combination of both. It has been shown that in catalytic compositions containing molybdenum oxide supported on silica, when there is increased surface coverage of the molybdenum oxide on the surface of the catalyst, the surface metal oxide molecules are forced to anchor on "strained" configurations that leads to increased reactivity. Tungsten oxide on silica remains the industrially preferred catalyst due to its stability, lifetime, and its insusceptibility to poisons and contaminants, which may be present in the feed. An embodiment of a metathesis catalyst described here includes catalytic tungsten oxide species supported on silica, denoted here as $WO_x/SiO_2$, which is prepared in the presence of a surfactant.

Disclosed here are methods of preparation of the $WO_x/SiO_2$ metathesis catalyst using a spray dryer. One such method includes the steps of synthesizing the catalyst using preformed silica, which has the desired properties for providing active sites for the butene to propylene metathesis reactions, and a polymeric surfactant to enhance the dispersion of the tungsten catalyst. In certain embodiments, the surfactant is a symmetric triblock copolymer, such as the Pluronic® P123 surfactant (available from BASF Corporation, headquartered in Florham Park, N.J., USA), which is a poly(ethylene glycol)-block-poly(propylene glycol)-block-poly(ethylene glycol) (PEG-PPG-PEG) copolymer. The triblock copolymer, PEG-PPG-PEG, constitutes of poly(ethylene oxide)(PEO) and poly (propylene oxide)(PPO) copolymers and exhibits hydrophobicity at temperatures above 288 Kelvin and solubility in water at temperatures below 288 Kelvin. This dual characteristic leads to formation of micelles consisting of PEO-PPO-PEO triblock copolymers. Pluronic® P123 surfactant has been used in the synthesis of mesoporous materials including FDU-14, a class of materials first synthesized at Fudan University in Shanghai, China. Dissolved Pluronic® P123 surfactant forms micelles that are used as the backbone to make structured mesoporous silica such as SBA-15. In contrast, disclosed here are uses of the triblock copolymer to facilitate the deposition of tungsten oxide on the silica support. In conventional synthesis, the surfactant is added to a metal precursor and this mixture is subject to thermal treatment. The metal precursor decomposes to generate a metal oxide. In the methods and compositions disclosed here, the surfactant was used to enhance the mixing between the silica support (e.g. CARiACT® silica) and the tungsten precursor, and also to improve the dispersion of tungsten oxide on the silica support upon thermal treatment. Surfactant properties, such as whether the surfactant is ionic, cationic or nonionic, play a role in the effectiveness of a polymeric surfactant. The use of a triblock copolymer enables an easy and reliable large scale method of preparation of the $WO_x/SO_2$ catalyst compositions. These methods also provide for uniform dispersion of the tungsten oxide on the surface of an inactive support. The triblock copolymer also enhanced the mixing of the tungsten precursor and $SiO_2$ mixtures. The tungsten precursor and $SiO_2$ mixtures were subjected to an extended mixing period to form a homogeneous mixture. In certain embodiments, the extended mixing period was three days.

The $WO_x/SiO_2$ catalytic compositions disclosed here exhibit a uniform distribution of the $WO_x$ on the surface of the silica support. The uniform distribution abates lateral interactions between the metal oxide particles and reduces crystal formation. Tungsten crystals are known to be inactive for metathesis. Furthermore, the catalyst synthesized by spray drying displayed great stability (especially at lower metal loading amounts and lower operating temperatures) and was shown to have significant selectivity towards propylene when compared to catalysts made using conventional synthesis approaches, such as the incipient wetness impregnation and the wet impregnation techniques.

Below are three formulas, which are referenced in this disclosure. These formulas define conversion X, conversion-C4 and selectivity:

$$X_i = \frac{\dot{n}_{i,in} - \dot{n}_{i,out}}{\dot{n}_{i,in}} = 1 - \frac{\dot{n}_{i,out}}{\dot{n}_{i,in}} \qquad \text{[Formula I]}$$

where, $X_i$ is the conversion of the 2-butenes (cis and trans) and $\dot{n}_{i,in}$ and $\dot{n}_{i,out}$ are the number of moles of 2-butenes (cis and trans) in and out of the reactor. The conversion values reported in the patent are the combined conversion of the cis- and trans-2-butenes.

$$\text{Conversion-C4} = \qquad \text{[Formula II]}$$
$$100 - (\text{CisButene Yield} + \text{TransButene Yield} +$$
$$\text{IsoButene Yield} + \text{1-Butene Yield})$$

$$\text{Selectivity} = \frac{\text{Yield of Product}}{\text{Conversion}} \times 100 \qquad \text{[Formula III]}$$

Embodiments of the synthesis methods include utilizing a spray dryer to prepare a metathesis catalyst for the catalytic conversion of a C$_4$ stream. In an embodiment, the WO$_x$/SiO$_2$ catalytic composition is used for the production of propylene from a feed containing 2-butenes (primarily cis- and trans-2-butenes). In an embodiment, the WO$_x$/SiO$_2$ catalytic composition is used for the production of propylene from a feed containing a mixture of 1-butene and 2-butene. In certain embodiments, the catalytic composition is synthesized by distributing tungsten oxide on a silica support in the presence of a triblock copolymer surfactant, such as Pluronic® P123 and using a spray dryer.

The preparation of the catalytic composition results in WO$_x$/SiO$_2$ catalysts that exhibit enhanced metathesis performance. The catalytic activity of the spray-dried WO$_x$/SiO$_2$ composition was evaluated in a fixed bed reactor and its performance was compared against other metathesis catalysts prepared via conventional synthesis methods. The spray-dried catalyst was highly active and stable, and performed superior to the catalysts that were prepared using the wet impregnation and the incipient wetness impregnation methods. Moreover, evaluation of the physical characteristics of the spray-dried catalyst revealed a uniform dispersion of the tungsten oxide on the surface of the silica support, which translated to greater conversions and greater propylene and ethylene yields. These WO$_x$/SiP$_2$ catalytic compositions are highly advantageous in the self- and cross-metathesis of butenes to propylene, and present a substantial improvement to the process using low cost butenes as feedstock. Thus, these catalytic compositions address the technological need for efficient conversion of low-value butenes to high-value propylene without the need for ethylene as feedstock. The WO$_x$/SiO$_2$ catalytic compositions can be utilized in processes for the selective production of propylene using a multiple-bed catalyst system.

Embodiments of the methods of preparation of the WO$_x$/SiO$_2$ catalytic compositions are easy to implement, and the resulting catalyst was more efficient and reliable than other metathesis catalysts prepared via conventional synthesis methods. The spray drying method to prepare these WO$_x$/SiO$_2$ catalytic compositions is scalable to an industrial level. Unlike conventional synthesis techniques that suffer from reduced catalyst activity when scaled up, this technique has proven to be reliable even when synthesizing 1 kilogram (kg) of catalyst. When conventional synthesis methods were used for the preparation of metathesis catalysts, scaling the amount of catalysts prepared from 2 grams to more than 20 grams resulted in non-uniform dispersion of tungsten. The performance of the catalyst was affected and the propylene yield was reduced. When the spray drying method as described here was utilized to scale the synthesis of the WO$_x$/SiO$_2$ catalyst, even up to 1 kg, the catalytic composition displayed uniform size, distribution, and morphology.

The WO$_x$/SiO$_2$ catalytic compositions also demonstrated stable catalytic conversion and olefin selectivity when utilized at lower temperatures and lower metal loading amounts, in the 3-8 wt % range. No variations were present in the performance of the catalyst from one batch to another—unlike conventional synthesis methods which were susceptible to this drawback. The conventional metathesis catalysts were not stable at temperatures of 450° C. and at lower metal loadings, such as 3-8%. Thus, the spray drying method of preparing the catalytic composition allowed for the synthesis of a robust and stable metathesis catalyst.

Embodiments of the methods to synthesize the WO$_x$/SiO$_2$ metathesis catalyst, as described here, achieve a better and more uniform dispersion of the tungsten on the silica support, which translates to improved performance and stability when compared to conventional synthesis methods. Examples of silica supports used in preparation of these catalytic compositions include mesoporous silica supports. The mesoporous silica catalysts may include an average pore diameter from about 2.5 nm to about 40 nm and a total pore volume of at least about 0.600 milliliter per gram (mL/g). In one or more embodiments, the average pore diameter of the silica support may range from about 2.5 nm to about 40 nm, or about 2.5 nm to about 20 nm, or about 2.5 nm to about 4.5 nm, or about 2.5 nm to about 3.5 nm, or about 8 nm to about 18 nm, or about 12 nm to about 18 nm. In further embodiments, the total pore volume may be from about 0.600 mL/g to about 2.5 mL/g, or about 0.600 mL/g to about 1.5 mL/g, or about 0.600 mL/g to about 1.3 mL/g, or about 0.600 mL/g to about 0.800 mL/g, or about 0.600 mL/g to about 0.700 mL/g, or about 0.900 mL/g to about 1.3 mL/g. Moreover, while broader ranges are contemplated, the silica support may, in one or more embodiments, include a surface area of about 250 square meters per gram (m$^2$/g) to about 600 m$^2$/g. In further embodiments, the silica support may have a surface area of from about 450 m$^2$/g to about 600 m$^2$/g, or about 250 m$^2$/g to about 500 m$^2$/g, or about 275 m$^2$/g to about 400 m$^2$/g, or about 275 m$^2$/g to about 350 m$^2$/g. In certain embodiments, these silica supports are free of extraneous metals or elements which might adversely affect the catalytic activity of the system. In certain embodiments, these silica supports contain less than 1 wt % of these extraneous metals or elements. One suitable embodiment of a silica support may be the Santa Barbara Amorphous (SBA-15) mesoporous silica molecular sieve. Alternatively, another suitable example is the CARiACT® silica support (commercially available from Fuji Silysia Chemical Ltd, headquartered in Aichi, Japan). In an embodiment, the greatest propylene yield was obtained when CARiACT® Grade Q-10 when used as a support for the tungsten-based catalyst. In an embodiment, the silica support used to manufacture the catalytic composition was CARiACT® Grade Q-10 particles that have an average pore diameter of about 10 nanometers, pore volume of 1 mL/g, a surface area of 300 m$^2$/g, and particle sizes ranging from 75-150 micrometers (μm). In an embodiment, the silica support used to manufacture the catalytic composition was CARiACT® Grade Q-10 particles with particle sizes ranging from 75-500 μm. Compositions and methods disclosed here utilize SiO$_2$ particles instead of other sources of silicon. Thus, the step of formation of SiO$_2$ was eliminated either prior to spray drying or during the spray drying process or during an additional calcination step. The initial provision of a SiO$_2$ support with optimal properties of surface area, pore diameter, and pore volume leads to the reliable formation of a uniform catalyst composition. The use of silicon dioxide precursors, such as tetraethyl orthosilicate, requires additional steps of formation of SiO$_2$ in the spray dryer and does not result in uniform support structures. Thus, the propylene selectivity and yield in the metathesis reactions are affected.

Various amounts of tungsten oxide can be loaded on the silica support to form the catalytic compositions. For example and not by way of limitation, the molar ratio of silica to tungsten oxide ranges from 5 to 60, or from 5 to 15, or from 20 to 50, or from 20 to 40, or from 25 to 35. Various compounds containing tungsten can serve as precursors to the catalytic compositions. Examples of suitable sources of tungsten oxide are ammonium metatungstate hydrate (commercially available from Sigma-Aldrich Corporation, headquartered in St. Louis, Mo., USA) or ammonium paratungstate (commercially available from Sigma-Aldrich Corporation, headquartered in St. Louis, Mo., USA). Conventional methods of synthesis of the catalytic compositions use ammonium metatungstate hydrate with about 99.99% purity. While this source was suitable for the wet impregnation and incipient wetness impregnation synthesis methods, this source can be expensive for the spray drying process. In certain embodiments using the spray drying process, ammonium metatungstate hydrate with about 85% purity (commercially available from Honeywell Fluka, headquartered in Seelze, Germany) served as the tungsten oxide source for the catalytic composition. In certain embodiments, the spray drying process can be carried out at about 200° C. to 300° C., or from about 250° C. to 285° C. In certain embodiments, the spray drying process is carried out at about 260° C. to 280° C. In certain embodiments, the spray drying process is carried out at about 250° C. to 275° C. All the catalysts were subsequently subject to calcination. In an embodiment, this calcination process is a two-step procedure. This process ensures the decomposition of the triblock copolymer, such as the Pluronic® P123 surfactant, and also the formation of stable and active tungsten oxide species from the tungsten precursor, such as ammonium metatungstate. In certain embodiments, calcination is carried out in the presence of one or more of the following gases: air, oxygen, hydrogen, and nitrogen. In certain embodiments, calcination is carried out at temperatures selected from 200° C. to 700° C. The thermal treatment conditions, including the type of gaseous environment and temperature, influence the tungsten oxide species that are formed. The type of tungsten oxide species affect the stability and metathesis activity of the catalyst composition, including the propylene yield. The two-step calcination process described here resulted in stable tungsten oxide phases for self- and cross-metathesis. The first step of the calcination process follows the thermal decomposition of ammonium metatungstate as it is converted to WON. In an embodiment, this first step is carried out at about 200° C.-250° C. in the presence of air. There is a significant weight loss of the tungsten precursor. The degradation of the tungsten precursor and conversion of the tungsten precursor to WOx continues until the second step which is carried out at about 500° C. to 600° C. at which the weight loss of the tungsten precursor is stabilized and active WOx species for metathesis are formed. In an embodiment, the catalyst composition is first subject to calcination at 250° C. for 2 hours and at 550° C. for 8 hours, with a ramping rate of 1° C. per minute until the first temperature is reached and 3° C. per minute until the second temperature is reached. The following examples are provided to illustrate the various embodiments, without any limitations to the scope of the disclosure.

EXAMPLES

Example 1

Preparation of Silica Supports

In a typical preparation of a silica support, the desired amount of CARiACT® Grade Q-10 was placed in a ceramic plate. The sample was then calcined at 200° C. for three hours and then at 575° C. for five hours, with a ramping rate of 3° C. per minute. Calcination of these samples was carried out in a VULCAN® 3-550 furnace (commercially available from Dentsply Ceramco, headquartered in York, Pa., USA).

Example 2

Preparation of Silica Support Impregnated with Tungsten Via Incipient Wetness Impregnation In a typical synthesis of the silica samples impregnated with a tungsten precursor, about 2 grams of the silica support (from Example 1) was placed in an 80 mL beaker. About 0.235 g of ammonium metatungstate hydrate (99.99% trace metals basis) was weighed out and mixed with 2 mL of deionized water. The solution was then added drop-wise to the silica support, and, about 5 drops were placed on the support. A glass rod was used to thoroughly mix the support. Following that, the catalytic composition was placed in a drying oven overnight at 80° C. The dried catalyst was calcined at 250° C. for 2 hours and at 550° C. for 8 hours, with a ramping rate of 1° C. per minute until the first temperature is reached and 3° C. per minute until the second temperature is reached. Calcination of these samples was carried out in a VULCAN® 3-550 furnace (commercially available from Dentsply Ceramco, headquartered in York, Pa. USA).

Example 3

Preparation of Silica Support Impregnated with Tungsten Via Wet Impregnation

About 2 grams of the silica support (from Example 1) and about 0.235 g of ammonium metatungstate (99.99% trace metals basis) were added to a round bottom flask. About 20 mL of deionized water was then added to the flask. A magnetic stir bar was added to the flask and the flask is placed on a stir plate that was programmed to run at 500 rpm, for roughly two hours. The magnetic stir bar was removed from the flask, and the flask was connected to a rotary evaporator. The conditions for operations of the rotary evaporator were: rotation set to 171 rpm, temperature of the water bath set to 80° C., vacuum set to 292 mbar, and the cooling liquid (50% water and 50% glycol) maintained at 6° C. Once all the water in the flask had evaporated, the flask was disconnected from the rotary evaporator and placed overnight in a drying oven which was operated at 80° C. Calcination of these samples was carried out in the VULCAN® 3-550 furnace. The dried catalyst was calcined at 250° C. for 2 hours and at 550° C. for 8 hours, with a ramping rate of 1° C. per minute until the first temperature is reached and 3° C. per minute until the second temperature is reached.

Example 4

Preparation of the $WO_x/SiO_2$ Catalytic Composition Using the Spray Drying Process About 100 grams of the CARiACT® Grade Q-10 silica was placed in a graduated cylinder and about 720 mL of water was added to the graduated cylinder. The mixture was stirred for approximately 30 minutes at about greater than 800 rpm to avoid the precipitation of the silica support at the bottom of the graduated cylinder. In another beaker, about 20 grams of a triblock copolymer, such as the Pluronic® P123 surfactant was mixed into a solution of 100 mL of water and 200 mL of ethanol, for approximately 30 minutes at high rpm until the surfactant was completely dissolved. A third mixture was prepared by mixing about 13.839 grams of the ammonium metatungstate hydrate precursor (85% $WO_3$)

and 30 mL of water until all the tungsten precursor was dissolved. Other solvents may be used as long as the triblock copolymer and the tungsten precursor form homogenous mixtures. When the spray dryer is operated at approximately 250° C., the temperature is around the flammability limits of ethanol vapor (as the spray dryer vaporizes all of the solvent). Thus, in certain instances, the use of ethanolic mixtures may be limited, as it could pose a safety hazard depending on the quantity of ethanol. In certain instances, from an operational standpoint, an aqueous mixture may be more economical as compared to an ethanolic mixture. This third aqueous mixture containing tungsten was added to the second mixture, which contains the triblock copolymer, such as the Pluronic® P123 surfactant. The tungsten-containing mixture is added to the second mixture only after the Pluronic® P123 surfactant had been dissolved. The continuous stirring of the Pluronic® P123-containing mixture is maintained at about 800 rpm during the addition of the tungsten-containing mixture. This mixture containing both tungsten precursors and Pluronic® P123 surfactant was then added to the first mixture that contains the silica support in water. The combined mixture was subject to continuous stirring at about 900 rpm for three days. The extended stirring period facilitated the mixing of the tungsten with the silica and also eliminated the precipitation of the silica prior to and during spray drying. Silica particles can clog the spray dryer nozzle if the silica particles are allowed to aggregate. After three days, the mixture had a cloudy and homogenous appearance.

The operating conditions (including temperature and flowrate) and the surface of the inside of the spray dryer (in terms of area and cleanness) determine the actual amount of tungsten oxide that is deposited on the silica support and the amount of silica that is left or lost inside the spray dryer. The catalyst yield in this Example was about 95%. A small amount of tungsten and silica adhered to the inside surface of the spray dryer, affecting the amount of tungsten loaded on the silica support. The amount of tungsten oxide present in the $WO_x/SiO_2$ catalytic composition was evaluated using elemental analysis methods, such as X-ray fluorescence (XRF) and inductively coupled plasma (ICP) analytical techniques.

The spray dryer used in these experiments was a GEA Niro MOBILE MINOR™ spray dryer for aqueous feeds, which is available from GEA Group Aktiengesellschaft, headquartered in Dusseldorf, Germany. The drying chamber in this instrument has the following dimensions: diameter of 793 mm and height of 660 mm cylindrical section with a 60 degree-cone bottom. Prior to operating the spray dryer, the inside chamber was thoroughly cleaned. After cleaning the chamber, the spray dryer was turned on and allowed to gradually heat, with the only input being deionized water. Once the temperature of the inside surface of the spray dryer reached 275° C. and stayed stabilized (stabilization conditions also included management of the temperature of the outlet and the flowrate of the inlet), the mixture containing tungsten, silica and Pluronic® P123 surfactant was supplied to the spray dryer instead of the deionized water.

The operating conditions for the spray drying can include a target pump rate of about 240 mL per minute of the mixture containing tungsten, silica, and Pluronic® P123 surfactant. In another example, the flowrate of the mixture fed to the spray dryer was constantly altered to control the exhaust temperature at a value below 110° C. The atomizer was operated at about 17 rpm and the temperature was about 105.6° C. The fan speed was set to 2009 rpm. The temperature of the inside surface of the spray dryer was maintained at 275° C.

Catalytic compositions can be retrieved from one or more locations in the spray drying unit. For example, while using a rotary spray dryer, samples were collected from two different points—one from the bottom of the spray dryer and the other one from the side of the spray dryer. The catalytic composition that is retrieved from the bottom of the spray dryer is referred to as the "heavy" fraction, because the silica particles that are collected there are heavier and slightly bigger in size. On the other hand, the catalytic composition that is collected from the side of the spray dryer is referred to as the "light" fraction because the silica particles in this section are lighter and are smaller in size. Particle size of the heavy and light fractions were analyzed using particle size analyzer from Horiba, Japan. The mean particle size for the light fraction was in the range from 750-900 nm and for the heavy fraction was in the range from 1000-1200 nm.

The amount of tungsten incorporated into the silica support also varies between the two fractions. For instance, in one preparation of the catalytic composition as described in Example 4, although there was 10% tungsten precursor in the solution, the catalytic composition in the heavy fraction contained only 2% of tungsten oxide and the catalytic composition in the light fraction contained about 18% of tungsten oxide. In another run, the catalytic composition in the light fraction contained about 6% tungsten oxide, as confirmed by XRF and ICP. To prepare a 6% $WO_x/SiO_2$ catalyst in the light fraction, about 8 grams of the ammonium metatungstate hydrate precursor (85% pure) was used in the process, as previously described.

Example 5

X-Ray Diffraction Analysis

Figure 2:
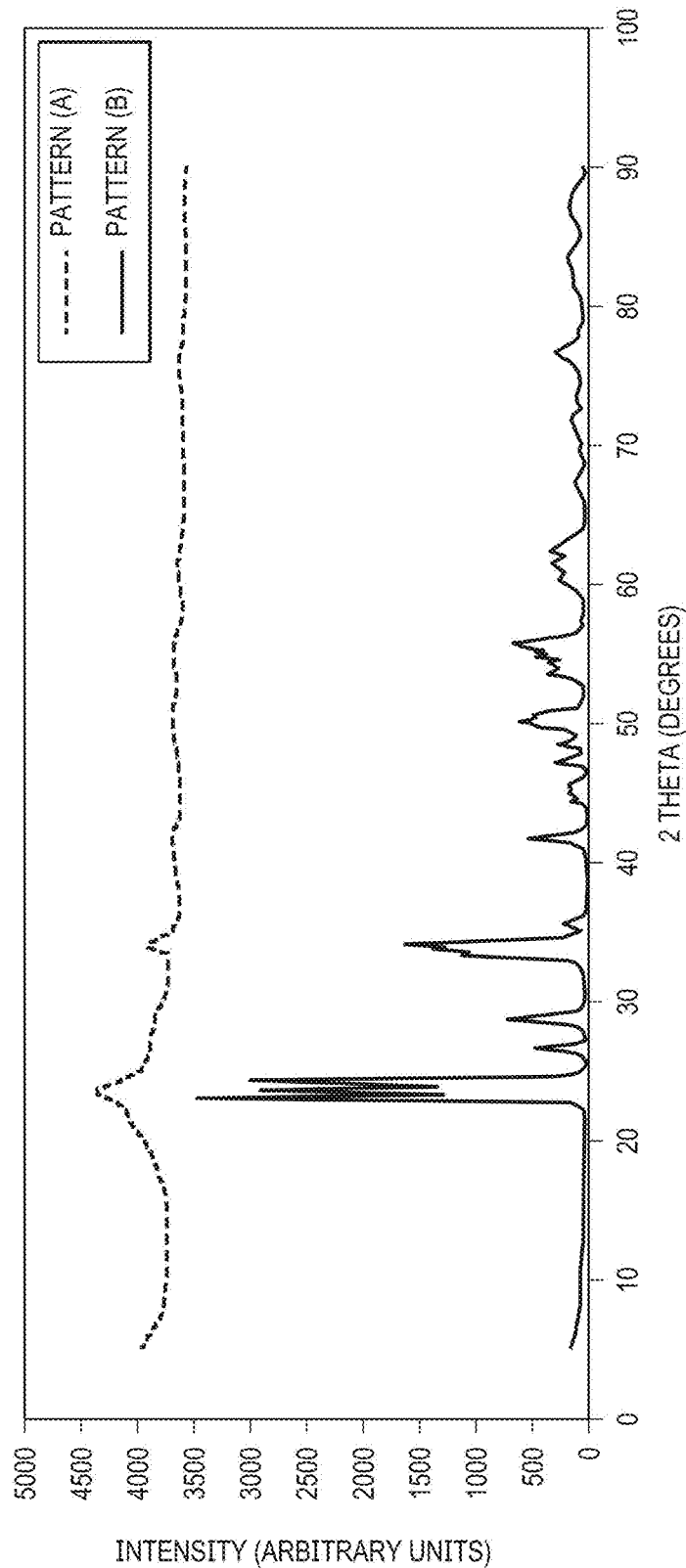
FIG. 2 provides the XRD patterns obtained following the analysis of the catalyst composition containing tungsten oxide on a silica support prepared by the incipient wetness impregnation method (Pattern A) and of tungsten oxide alone without any silica support (Pattern B) prepared by thermal treatment of the tungsten precursor used in this disclosure.
Figure 3:
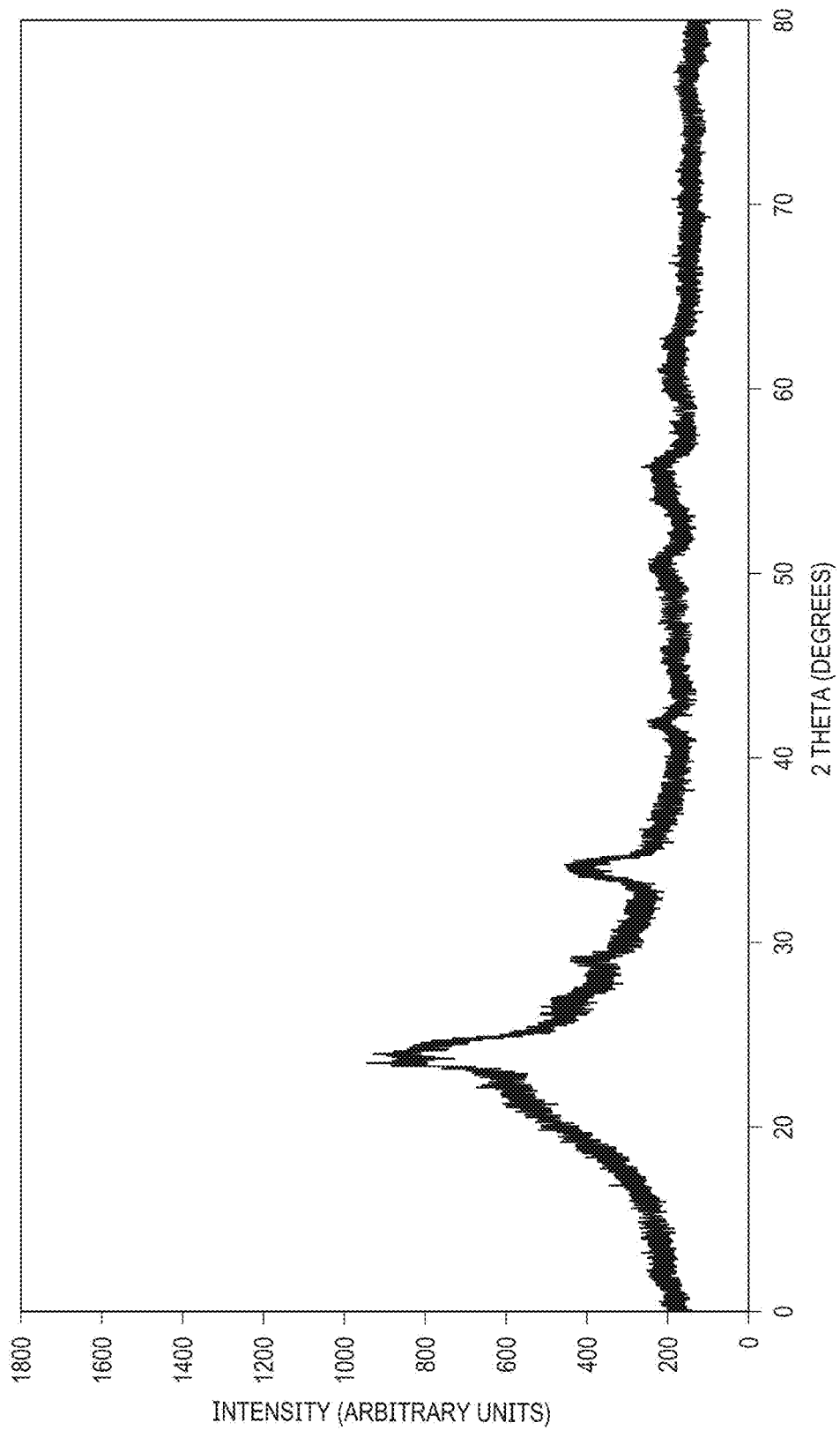
FIG. 3 is the XRD pattern obtained following the analysis of the catalyst composition containing tungsten oxide on a silica support prepared by the wet impregnation or the rotary vapor method.
Figure 4:
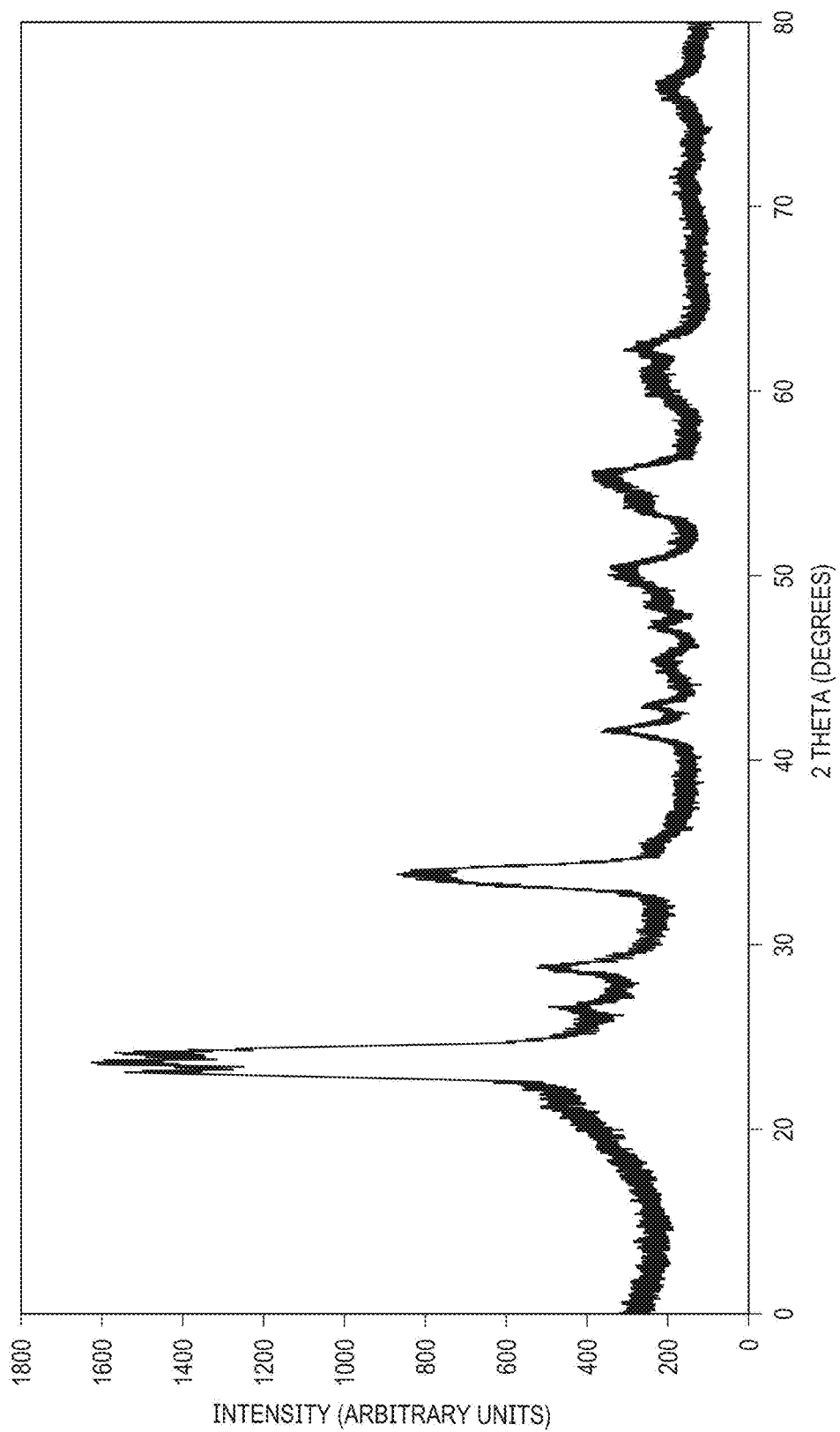
FIG. 4 is the XRD pattern obtained following the analysis of the catalyst composition containing tungsten oxide on a silica support prepared by the spray drying method.

The physical properties of the $WO_x/SiO_2$ catalyst composition prepared by the spray drying method described in Example 4 were compared to physical properties of the tungsten oxide on silica supports prepared by conventional methods. The XRD data were collected using D4 Endeavor X-Ray Diffractometer from Bruker AXS GmbH (Karlsruhe, Germany) and analyzed using DIFFRAC.EVA V4.1.1 version (available from Bruker), which had an in-built PDF library to match the perfect scan. Analyses were carried out at room temperature in the two-theta range from 20° to 80°. FIG. 1 is the XRD pattern obtained following the analysis of the silica supports, with no tungsten. The broad peak from a 2-theta value of 15° to approximately 30° is due to the silica support. FIG. 2 provides the XRD patterns obtained following the analysis of the catalyst composition containing tungsten oxide on a silica support prepared by the incipient wetness impregnation method (Pattern A) and of tungsten oxide alone without any silica support (Pattern B) prepared by thermal treatment of the tungsten precursor used in this disclosure. This catalyst contained about 10% tungsten oxide. FIG. 3 shows the XRD pattern obtained following the analysis of the catalyst containing tungsten oxide on a silica support prepared by the wet impregnation or the rotary vapor method. FIG. 4 shows the XRD pattern obtained following the analysis of the catalyst containing tungsten oxide on a silica support prepared by the spray drying method (6% $WO_x/SiO_2$).

The activity of the supported $WO_x/SiO_2$ catalyst is directly related to the amount and concentration of surface $WO_x$ sites. Essentially, increasing the surface $WO_x$ sites by 2 to 8 $WO_x$ wt % increases the reaction rate, which ultimately increases the propylene yield. After a critical value, no increase in propylene yield is observed and in fact if the tungsten amount is drastically increased beyond that point, a decrease in propylene is observed. Typically, three types of tungsten species form in tungsten-based catalysts: surface tetrahederal tungsten species, surface octahedral polytungstate species, and $WO_3$ crystallines. The first two species have been shown to be active for metathesis, while the crystalline $WO_3$ species have been shown to be not active. The two active tungsten species for metathesis (tetrahedral and octahedral) are generally present when the $WO_x$ content is in the range of 3 to 15 wt %. While the crystalline $WO_3$ phase is not active for metathesis, it does nevertheless alter the acid sites on the catalyst, causing other byproducts and side reactions. At high tungsten loading values, the crystalline $WO_3$ phase becomes apparent and can be seen in the XRD (in the form of sharp peaks referring to the tungsten oxide phase). While $WO_3$ is the common phase for tungsten oxide, there are other tungsten oxide phases which may be present in the catalyst, too.

FIG. 1 shows the amorphous nature of silica. FIG. 2 shows two patterns: Pattern [A] corresponds to the tungsten precursor (ammonium metatungstate) after it was heated to 550° C. (using the same calcination procedure as $WO_3/SiO_2$ via incipient wetness impregnation (Example 2) to yield tungsten oxide (WOx) and Pattern [B] corresponds to the tungsten oxide alone without any silica support. Once tungsten is added on the silica support, the XRD patterns show the formation of tungsten oxide in all three figures: FIG. 2 (10% $WO_x/SiO_2$—incipient wetness), FIG. 3 (10% $WO_x/SiO_2$—wet impregnation) and FIG. 4 (6% $WO_x/SiO_2$—spray-dried). The sharp peaks in the XRD figures correspond to $WO_x$ on the surface of the catalyst. Sharper peaks correspond to more crystalline structures. The intensity of the peaks is proportional to the tungsten oxide content on the surface of the catalyst. Proper dispersion of the tungsten on the silica support is important for the metathesis reaction. The acidity of the catalyst surface as well as amount of tungsten on the surface of the catalyst are also important factors influencing the metathesis activity.

Example 6

Analysis of the Surface Area and Pore Volume

Differences in surface area and porosity of the catalyst compositions can greatly influence performance characteristics. The $WO_x/SiO_2$ catalyst composition prepared by the spray drying method described in Example 4 was subjected to surface area and porosity analysis, along with the silica supports with tungsten oxide prepared by conventional methods. Specific surface area of the various samples was determined by the Brunauer, Emmett and Teller (BET) technique that utilizes low temperature adsorption of nitrogen after calcination of the catalyst samples in air. Table 1 summarizes the BET surface area ($m^2/g$) and pore volume (mL/g) of the silica support without any tungsten oxide and the three catalyst samples with tungsten oxide prepared via different techniques.

TABLE 1

| Sample | BET Surface Area ($m^2/g$) | Pore Volume (mL/g) |
| --- | --- | --- |
| 100% $SiO_2$ | 304.41 | 1.13 |

TABLE 1-continued

| Sample | BET Surface Area ($m^2/g$) | Pore Volume (mL/g) |
| --- | --- | --- |
| 10% $WO_x/SiO_2$ (incipient wetness impregnation method) | 274.35 | 0.81 |
| 10% $WO_x/SiO_2$ (wetness impregnation method) | 222.61 | 1.104 |
| 6% $WO_x/SiO_2$ (Spray-dried- Light Fraction) | 231.01 | 1.11 |

The surface area and pore volume of the tungsten-loaded silica decreased slightly after the tungsten oxide is loaded on the support. The silica support without tungsten has a greater surface area of 304.41 $m^2/g$ and pore volume of 1.13 mL/g, as compared to the tungsten-loaded silica compositions. Upon loading with tungsten oxide on silica, the surface area of the overall silica surface decreases, as seen in Table 1, due to formation of small crystalline $WO_3$ on surface of silica. Very little change in the pore volume was observed upon loading of $WO_3$ on silica using wetness impregnation method and spray drying method, which suggests the loading was perfect on the surface without occupying the much of the pores. There is considerable reduction in pore volume after loading the silica using incipient wetness impregnation that could be due to incorporation of $WO_3$ inside the pores. Thus, the catalytic composition prepared by spray drying has a balanced BET surface area and pore volume, when compared to the catalysts prepared by other methods.

Example 7

Energy Dispersive Spectroscopy Analysis

Figure 5A:
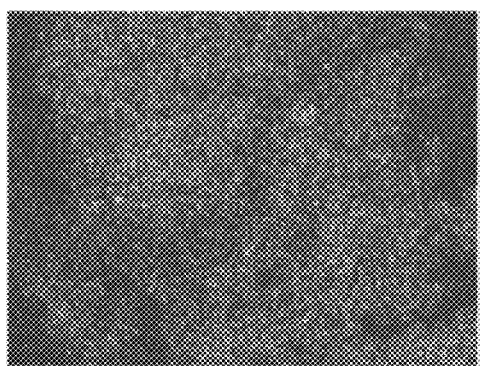
FIGS. 5A and 5B are the energy dispersive spectroscopy (EDS) images of the silica supports with tungsten oxide prepared by incipient wetness method (FIG. 5A) and the wet impregnation method (FIG. 5B).
Figure 5B:
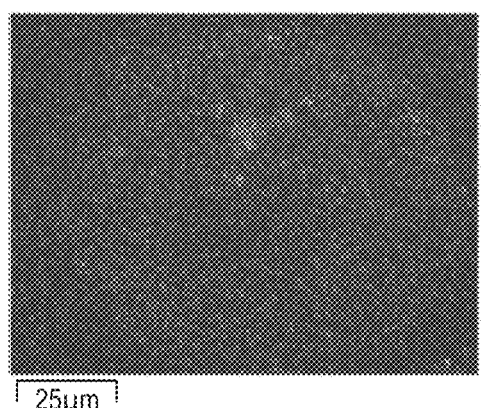
Figure 5C:
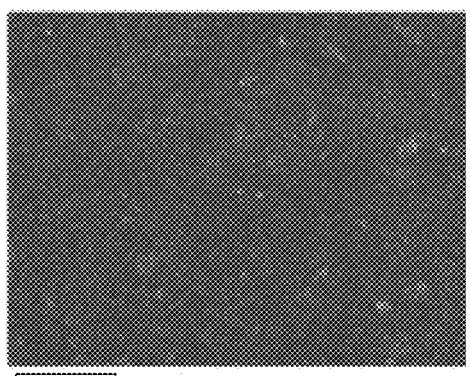
FIG. 5C is the EDS image of the catalyst composition containing tungsten oxide on a silica support, prepared by the spray drying method.

The $WO_x/SiO_2$ catalyst composition prepared by the spray drying method described in Example 4 was subjected to energy dispersive spectroscopy (EDS-SEM) and scanning electron microscopy (SEM) analysis along with the silica supports with tungsten oxide prepared by conventional methods. FIGS. 5A and 5B are the EDS-SEM images of the silica supports with tungsten oxide prepared by incipient wetness method (FIG. 5A) and the wet impregnation method (FIG. 5A). FIG. 5C is the EDS-SEM image of the $WO_x/SiO_2$ catalyst composition prepared by the spray drying method. The tungsten oxide was more uniformly distributed on the silica support in FIG. 5C (the spray-dried catalyst) as compared to the samples in FIGS. 5A and 5B, and this uniform dispersion translates to better performance of that $WO_x/SiO_2$ composition as a catalyst.

Example 8

Evaluation of Catalyst Performance

Samples from the two fractions of the $WO_x/SiO_2$ catalyst composition prepared by the spray drying method described in Example 4 were evaluated for catalytic performance, along with samples of the $WO_x/SiO_2$ catalysts prepared by conventional techniques.

Figure 6:
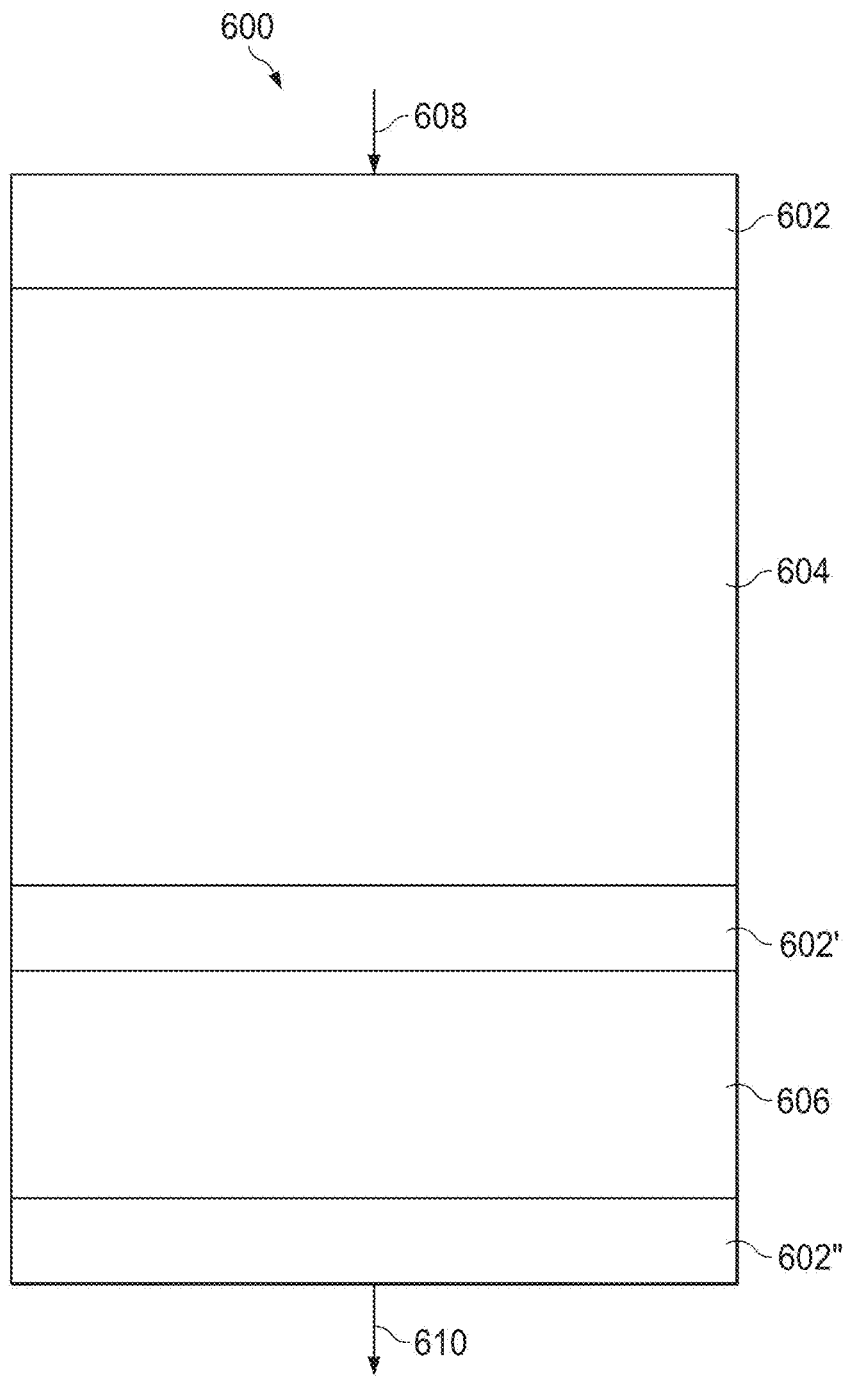
FIG. 6 is a diagrammatic representation of a reactor constructed to evaluate the performance of a catalyst composition.

The activity and selectivity of these different preparations were evaluated in a fixed bed continuous flow reactor (such as the reactors available from Autoclave Engineers headquartered in Houston, Tex., USA). A diagrammatic representation of the reactor used for catalyst performance is shown in FIG. 6. The reactor 600 has three layers of quartz wool 602, 602', and 602" separating the catalyst bed 604 from the silicon carbide layer 606. About 2 mL of the catalyst samples was packed in the reactor tubes with Grade 20 Silicon Carbide at the bottom of the reactor. The catalysts were pretreated/activated by passing an inert gas, such as nitrogen, through inlet 608. Nitrogen gas helps to get rid of moisture, and gas is supplied to the reactor at about 25 standard cubic centimeter per minute (sccm) at 550° C. for about 60 minutes. The temperature was then changed to the desired reaction temperature. A feed of 2-butene (5 mL/min) along with nitrogen as diluent (25 mL/min) was supplied to the reactor at a gas hourly space velocity (GHSV) of 900 per hour ($h^{-1}$). The quantitative analysis of the reaction products, exiting the reactor via outlet 610, was carried out using an in-line gas chromatograph, available from Agilent Technologies, headquartered in Santa Clara, Cali., USA. The Agilent GC-7890B chromatograph has a 50 m×0.53 mm×15 microns high performance alumina-potassium chloride (HP-Al/KCl) column. The gas chromatograph is equipped with a flame ionization detector (FID) to measure the organic species. Furthermore, the amount of tungsten in each sample was confirmed and characterized using both XRF and ICP.

The catalysts loaded in the reactor were heavy and light fractions containing different amounts of tungsten oxide loaded onto a silica support in the presence of the surfactant and prepared using the spray drying process of Example 4. The catalyst fractions were tested at 550° C. for 5 hours. The values shown in the Table 2 below are the averaged values (n=6). The heavy fraction of the $WO_x/SiO_2$ catalyst retrieved from the bottom of the spray dryer yielded about 22 mol % of propylene at lower tungsten loading on the silica support, between 2-3%. In comparison, the light fraction of the $WO_x/SiO_2$ catalytic composition, collected from the side of the spray dryer, yielded about 24-29 mol % of propylene at a greater tungsten loading on the silica support, between 6-25%.

TABLE 2

| Spray Drying | Propylene Yield (mol. %) |
| --- | --- |
| 2% $WO_x/SiO_2$ - Spray-Drying - Heavy | 21.44 |
| 3% $WO_x/SiO_2$ - Spray-Drying - Heavy | 21.82 |
| 6% $WO_x/SiO_2$ - Spray-Drying - Light | 28.54 |
| 18% $WO_x/SiO_2$ - Spray-Drying - Light | 24.85 |
| 25% $WO_x/SiO_2$ - Spray Drying - Light | 24.14 |

Other experiments indicate that metathesis activity remains constant for the $WO_x/SiO_2$ catalytic compositions with 6 to 15 wt % of tungsten oxide supported on silica, i.e., the propylene yield and selectivity does not change significantly. Experiments were conducted to analyze the stability of the catalyst. The 6% $WO_x/SiO_2$ obtained as the light fraction from the spray dryer was used as catalyst in a metathesis reaction run for 15 consecutive hours at 550° C. Surprisingly, there was no change in the yield or conversion rate for the entire time of the run.

The light fraction containing 6% $WO_x/SiO_2$ was evaluated for catalytic performance along with samples of silica supports with tungsten oxide prepared by conventional methods. The activity and selectivity of these different preparations were evaluated in a fixed bed continuous flow reactor under conditions, as previously described. The catalyst fractions were pretreated/activated by passing nitrogen gas at about 25 sccm at 550° C. for about 60 minutes. A feed of 2-butene (5 mL/min) along with nitrogen as diluent (25 mL/min) was supplied to the reactor at a gas hourly space velocity (GHSV) of 900 per hour ($h^{-1}$). The reaction products were analyzed by an in-line gas chromatograph, equipped with a flame ionization detector (FID) to measure the organic species.

Table 3 summarizes the yields, conversion, and selectivity of the three catalyst preparations that were prepared via different techniques. All three reactions were run at 550° C. for five hours. The reported numbers in the table are the averaged values for the 5 hour run (n=6).

TABLE 3

| Sample | Ethylene mol % | Propylene mol % | C5 mol % | C6+ mol % | Conversion | Ethylene Selectivity | Propylene Selectivity |
| --- | --- | --- | --- | --- | --- | --- | --- |
| 10% $WO_x/SiO_2$ (incipient wetness impregnation method) | 3.356 | 25.325 | 21.65 | 10.08 | 71.67 | 4.683 | 35.337 |
| 10% $WO_x/SiO_2$ (wetness impregnation method) | 4.409 | 27.561 | 19.90 | 9.77 | 73.29 | 6.016 | 37.606 |
| 6% $WO_x/SiO_2$ (Spray-dried-Light Fraction) | 5.947 | 28.578 | 22.19 | 10.15 | 79.23 | 7.506 | 36.068 |

The spray-dried catalyst composition (light fraction) consistently performed better than the catalysts prepared by the other conventional methods. Moreover, the spray-dried catalyst performs better than the other catalyst preparations despite having lower amount of tungsten oxide (as confirmed by XRF and ICP). Furthermore, the uniform dispersion of the tungsten increased the propylene and ethylene yields, and also increased the conversion of the butene feed by 10%, without increasing the $C_5$ and $C_{6+}$ byproducts significantly.

Example 9

Lower Metal Loading

To magnify the effect of the synthesis method on performance, three catalysts preparations were synthesized and were loaded with 3% tungsten oxide, which is lower than the optimal range of metal oxide loading for metathesis. The amount of tungsten in each catalyst was confirmed using XRF and ICP. These catalysts were run for 15 hours at 550° C. The propylene yield for three catalysts all loaded with 3% tungsten oxide is shown in Table 4.

TABLE 4

| TOS (hrs:mins:sec) | 3% WO$_x$/SiO$_2$ - Wet Impregnation | 3% WO$_x$/SiO$_2$ - Incipient Wetness | 3% WO$_x$/SiO$_2$ - Spray-Drying |
|---|---|---|---|
| 0:32:10 | 11.17 | 0.62 | 14.31 |
| 1:18:24 | 3.79 | 0.37 | 12.22 |
| 2:04:43 | 2.45 | 0.25 | 15.07 |
| 2:50:59 | 8.00 | 0.34 | 21.25 |
| 3:37:13 | 11.02 | 0.38 | 22.23 |
| 4:23:34 | 12.56 | 0.38 | 22.56 |
| 5:09:49 | 12.63 | 0.37 | 22.68 |
| 5:56:03 | 12.83 | 0.36 | 22.85 |
| 6:42:20 | 12.45 | 0.35 | 22.82 |
| 7:28:35 | 12.03 | 0.35 | 22.69 |
| 8:14:53 | 11.15 | 0.33 | 22.54 |
| 9:01:09 | 9.74 | 0.28 | 22.60 |
| 9:47:25 | 10.04 | 0.31 | 22.54 |
| 10:33:41 | 11.54 | 0.31 | 20.78 |
| 11:19:58 | 13.31 | 0.31 | 20.99 |
| 12:06:11 | 14.24 | 0.31 | 20.13 |
| 12:52:27 | 14.27 | 0.30 | 20.65 |
| 13:38:43 | 14.00 | 0.26 | 20.76 |
| 14:24:59 | 12.93 | 0.27 | 21.12 |

The catalyst prepared by the spray-dried process and utilizing the surfactant performed almost twice as better than the other catalysts at lower metal loading amounts and was stable in its catalytic activity. This is due to a uniform distribution of the tungsten oxide on the surface of the catalyst facilitated by the surfactant.

It should be understood that any two quantitative values assigned to a property may constitute a range of that property, and all combinations of ranges formed from all stated quantitative values of a given property are contemplated in this disclosure. Having described the subject matter of the present disclosure in detail and by reference to specific embodiments, it is noted that the various details described in this disclosure should not be taken to imply that these details relate to elements that are essential components of the various embodiments described in this disclosure, even in cases where a particular element is illustrated in each of the drawings that accompany the present description. Further, it will be apparent that modifications and variations are possible without departing from the scope of the appended claims.

What is claimed is:

1. A method for the preparation of a spray-dried metathesis catalyst composition, the method comprising:
    combining a tungsten precursor with a surfactant to form a first mixture;
    contacting the first mixture with a second mixture containing a silica support under conditions of constant stirring to form a third mixture containing the tungsten precursor loaded on the silica support, wherein the silica support comprises mesoporous silica supports, wherein the mesoporous silica support comprises SiO$_2$; and
    subjecting the third mixture to a spray drying process to obtain a spray-dried metathesis catalyst composition containing tungsten oxide loaded on the silica support.

2. The method of claim 1, wherein the silica support comprises preformed silica particles.

3. The method of claim 1, wherein the surfactant is a poly(ethylene glycol)-block-poly(propylene glycol)-block-poly(ethylene glycol) copolymer.

4. The method of claim 1, wherein the tungsten precursor contains ammonium metatungstate.

5. The method of claim 1, wherein the tungsten precursor contains ammonium paratungstate.

6. The method of claim 1, wherein the tungsten oxide loaded on the silica support of the spray-dried metathesis catalyst ranges from 2 to 25 weight percent.

7. The method of claim 1, wherein the tungsten oxide loaded on the silica support of the spray-dried metathesis catalyst ranges from 6 to 15 weight percent.

8. The method of claim 1, wherein the tungsten oxide loaded on the silica support of the spray-dried metathesis catalyst is about 6 weight percent.

9. The method of claim 1, wherein the spray drying process includes supplying the third mixture to a spray dryer at a temperature at about 250-300° C.

10. A method for production of propylene, the method comprising:
    contacting a hydrocarbon feedstock containing butenes under metathesis reaction conditions with a catalyst containing tungsten oxide on a silica support to produce a product stream containing propylene, the catalyst having been prepared by a spray drying process, wherein the silica support comprises mesoporous silica supports, wherein the mesoporous silica support comprises SiO$_2$; and
    fractionating the product stream to form a propylene-rich stream.

11. The method of claim 10, wherein the hydrocarbon feedstock contains 2-butene.

12. The method of claim 10, wherein the silica support comprises preformed silica particles.

13. The method of claim 10, wherein the catalyst is pretreated by exposure to nitrogen gas before being contacted with the hydrocarbon feedstock.

14. The method of claim 10, wherein the spray drying process includes contacting the silica support with a tungsten precursor in the presence of a surfactant.

15. The method of claim 14, wherein the surfactant is a poly(ethylene glycol)-block-poly(propylene glycol)-block-poly(ethylene glycol) copolymer.

16. The method of claim 10, wherein the tungsten precursor contains ammonium metatungstate.

17. The method of claim 10, wherein the tungsten precursor contains ammonium paratungstate.

18. The method of claim 10, wherein the tungsten oxide loaded on the silica support ranges from 2 to 25 weight percent.

19. The method of claim 10, wherein the tungsten oxide loaded on the silica support ranges from 6 to 15 weight percent.

20. The method of claim 10, wherein the tungsten oxide loaded on the silica support is about 6 weight percent.

* * * * *